United States Patent [19]

Sawchuk et al.

[11] Patent Number: 4,818,406

[45] Date of Patent: Apr. 4, 1989

[54] BIOLOGICAL DEGRADATION OF CHEMICALS BEARING AN OXYDIBENZENE NUCLEUS

[75] Inventors: David L. M. Sawchuk, Sarnia, Canada; Ronald H. Olsen, Ann Arbour, Mich.

[73] Assignee: Polysar Limited, Sarnia, Canada

[21] Appl. No.: 933,894

[22] Filed: Nov. 24, 1986

[51] Int. Cl.$^4$ .............. C02F 3/00; C12R 1/38
[52] U.S. Cl. .................. 210/611; 210/626; 210/909; 435/262; 435/264; 435/281; 435/282; 435/874
[58] Field of Search .............. 435/262, 264, 875, 280, 435/281, 282, 30, 42, 874; 210/611, 601, 615, 626, 909; 260/504 R, 504 S

[56] References Cited

U.S. PATENT DOCUMENTS

| | | | |
|---|---|---|---|
| 4,332,904 | 6/1982 | Kurane et al. | 435/262 |
| 4,440,644 | 4/1984 | Mudder et al. | 435/262 |
| 4,508,824 | 4/1985 | Olsen | 435/874 |
| 4,511,657 | 4/1985 | Colaruotolo et al. | 435/262 |
| 4,535,061 | 8/1985 | Chakrabarty et al. | 435/262 |
| 4,537,682 | 8/1985 | Wong-Chong | 210/611 |
| 4,562,156 | 12/1985 | Isbister et al. | 435/874 |
| 4,745,064 | 5/1988 | Cook et al. | 435/42 |

FOREIGN PATENT DOCUMENTS

| | | | |
|---|---|---|---|
| 0148285 | 11/1981 | Japan | 435/874 |
| 0612958 | 6/1978 | U.S.S.R. | 435/262 |
| 0962304 | 9/1982 | U.S.S.R. | 435/874 |

OTHER PUBLICATIONS

Kunicka-Goldfinger et al, ACTA Microbiologica Polonica, vol. 29, No. 4, 1980, pp. 407-412.
Hill et al, Biotechnology and Bioengineering, vol. XVII, 1975, pp. 1599-1615.

*Primary Examiner*—Robert J. Warden
*Assistant Examiner*—Florina B. Hoffer
*Attorney, Agent, or Firm*—Stevens, Davis, Miller & Mosher

[57] ABSTRACT

A bacterium has been isolated which is capable of degrading surfactants having an oxydibenzene nucleus, such as sodium dodecyl oxydibenzene disulfonate. Accordingly, it may be used in biological wastewater treatment plants to remove the surfactant. The preferred bacterium is *Pseudomonas cepacia* OLSA100.

4 Claims, No Drawings

BIOLOGICAL DEGRADATION OF CHEMICALS BEARING AN OXYDIBENZENE NUCLEUS

FIELD OF THE INVENTION

This invention relates to microbial degradation particularly of chemical products contained in petrochemical wastewater.

BACKGROUND OF THE INVENTION

As chemical compounds foreign to the biosphere are produced and discharged into the environment, the risk of accumulation to toxic levels becomes a concern. The magnitude of the risk depends to a large extent on the biodegradability of the compound which, in turn, is dependent to some extent on the inherent or adapted ability of microorganisms to assimilate the compound or its components or derivatives. Many of these chemical compounds are resistant to biodegradation. However, some of these new compounds are biodegraded in relatively short periods by soil bacteria which apparently adapt to metabolizing the new substrates. Such adapted strains that may be isolated from nature, however, may have growth characteristics which do not promote their development in sufficient numbers to assure significant degradation of a target compound molecule.

Of particular concern herein are chemical compounds which are discharged into industrial effluent streams. Without proper treatment, the compounds may be ultimately discharged to receiving waters. A majority of the organic compounds are now degraded using biological treatment plants, thereby lowering the total organic carbon in the final effluent which is discharged to a receiving waterway. The ability of the microbial flora to digest the raw wastewater components is challenged when new compounds foreign to them are introduced. If they are unable to metabolize these new compounds, it is likely that the compound will be discharged without modification, a result which can be serious if the compound is toxic or can be converted to become toxic by other environmental components.

SUMMARY OF THE INVENTION

From one of its broadest aspects, the present invention is concerned with biodegradation of compounds having the oxydibenzene nucleus of formula I

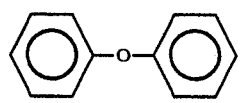

(I)

More particularly, the invention is concerned with surfactants conforming to the above general formula I wherein the benzenes are substituted by hydrophilic radicals and by hydrophobic radicals to confer the polarity required of a surfactant. Such compounds will therefore conform to the general formula II

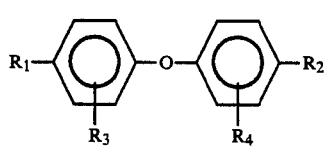

(II)

wherein $R_1$ and $R_2$ are independently selected from hydrogen and a $C_8$–$C_{20}$ alkyl radical and $R_3$ and $R_4$ are independently selected hydrogen and a hydrophilic radical preferably selected from a sulfonate radical and a sulfate radical, where one of $R_1$ and $R_2$ and one of $R_3$ and $R_4$ is other than hydrogen.

Of particular concern herein are the alkyl sulfonated biphenyl compounds conforming to general formula II which are used in the production of synthetic polymers. A representative such compound is sodium dodecyl oxydibenzene disulfonate (DODBS) which has the formula

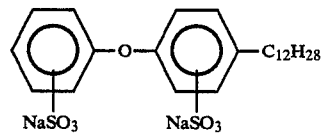

The compounds defined above all possess the oxydibenzene nucleus which is of particular concern from an environmental viewpoint. It is therefore desirable to limit discharge of these compounds to the environment.

The surfactants conforming to this formula i.e. of formula II, are of additional concern given their propensity for foaming when aerated. The problem is particularly acute in aerobic wastewater treatment facilities where constant aeration of the tank bearing activated sludge (hereinafter referred to as the aeration tank) is required to maintain the treatment process. Influent containing the surfactants can foam to an extent which can lift the microbially active floc out of the aeration sludge tank and into discharge spillways. Not only are the bacteria lost but the surfactants may be discharged untreated. Foaming is also aesthetically undesirable.

From another aspect, therefore, the present invention is concerned with providing a means for degrading the compounds defined above not only to satisfy environmental concerns but also to improve the efficient operation of biological treatment facilities into which the surfactant compounds described above are discharged.

There has now been identified and isolated a novel bacterium which is able to degrade compounds having the formulae defined above. This bacterium has the identifying characteristics of a *Pseudomonas cepacia* archetype catalogued by the American Type Culture Collection in Rockville, Md., U.S.A. under accession number 25609. The archetype bacterium will not readily utilize oxydibenzene disulfonate as a sole carbon source and will only demonstrate a partial degradation of oxydibenzene compounds after long lag times, e.g. 2–6 days. The novel bacterium of the present invention has the additional characteristic of utilizing sodium dodecyl oxydibenzene disulfonate as a sole carbon source when cultured in the presence of other typically required nutrients. This novel strain is referred to hereinafter as *P. cepacia* OLSA100. Specimens of *P. cepacia* OLSA100 have been deposited in the American Type Culture Collection, Rockville, Md., under accession number 53554.

*P. cepacia* OLSA100 was selected from a sludge sample obtained from the aerobic wastewater treatment facility operated by Polysar Limited in Sarnia, Ontario. Bacteria contained in the sample were screened for growth on a medium whose only carbon source was the surfactant sodium dodecyl oxydibenzene disulphonate (DODBS). As a subsequent criterion, only that colony exhibiting superior growth at ambient temperature was selected, isolated and identified and subsequently labelled *P. cepacia* OLSA100.

While it is generally recognized that *P. cepacia* are extremely versatile nutritionally, it is believed that the novel bacterium OLSA100 is a strain having properties heretofore unknown. Other *P. cepacia* strains, including ATCC 25609 and ATCC 25416 fail to exhibit substantive growth on the selection medium used.

The cause of the modification which resulted in the novel strain is believed to have been contained in the wastewater from which the strain was isolated. Prior to isolation, the activated slude had been subjected to varying concentrations of DODBS suggesting that repeated exposure to this surfactant encouraged acclimatization. Now having isolated the bacterium, however, it is possible to manipulate its presence in wastewater treatment facilities in order to degrade DODBS contained in the wastewater.

Accordingly, the present invention comprises a biologically pure culture of a bacterium having the identifying characteristics of *Pseudomonas cepacia* and which exhibits growth at ambient temperatures on nutrient medium containing only sodium dodecyl oxydibenzene disulfonate as a carbon source. Preferably, the bacterium is *P. cepacia* OLSA100 including any clones and sub-clones thereof.

The present invention further comprises a process for degrading compounds of formula II

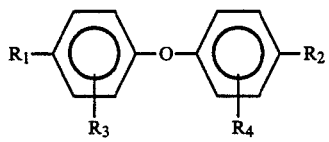

(II)

wherein $R_1$ and $R_2$ are independently selected from hydrogen and a $C_8$–$C_{20}$ alkyl radical and $R_3$ and $R_4$ are independently selected hydrogen and a sulfonate radical, wherein at least one of $R_1$ and $R_2$ and one of $R_3$ and $R_4$ is other than hydrogen which comprises growing the bacteria in the presence of said compound under aerobic conditions. Preferably, the compound is DODBS (wherein, in formula II above, one of $R_1$ and $R_2$ is hydrogen and the other is $C_{12}H_{25}$ and both $R_3$ and $R_4$ are the sodium sulfonate radical).

DESCRIPTION OF THE PREFERRED EMBODIMENTS

The process aspect of the invention has been developed particularly with respect ot the degradation of DODBS using *P. cepacia* OLSA100 in an aerobic, biological, wastewater treatment facility.

The process entails seeding activated sludge with a population of the bacteria sufficient to degrade a desired amount of DODBS.

The size of the bacterial inoculum seeded in the sludge will depend on several factors, as is usual, including the resident time of the wastewater containing the DODBS, the concentration of the DODBS in the wastewater, the availability of other carbon sources and the interaction of the microbial flora.

*P. cepacia* OLSA100 is able to function without significant, harmful interference in the presence of many bacteria indigenous to conditioned activated sludge. The viability of the novel bacteria in any selected sludge is easily confirmed using conventional experimental procedures.

In addition, and surprisingly, it is evident that despite the availability of other carbon sources such as glucose which are generally accepted as being preferred substrates by microbes, DODBS is degraded by the *P. cepacia* OLSA100 bacteria. It appears, therefore that DODBS is not only metabolized by *P. cepacia* OLSA100, but the bacterium's activity is not diminished by or in the presence of other substrates or carbon sources. DODBS has been successfully degraded by the *P. cepacia* OLSA100 bacterium at concentration as low as 0.2 ppm. For practical purposes i.e. on an industrial scale, such low concentrations are rarely encountered. The upper limit of DODBS concentration tolerable by the *P. cepacia* OLSA100 bacterium is quite high, with indications that growth occurs at 2,000 ppm.

Given these observations, it will be readily appreciated that *P. cepacia* OLSA100 is ideally suited for application in a wastewater treatment plant of industrial proportion. The bacterium is able to tolerate DODBS concentrations in a range which it can normally be expected to encounter in industrial treatments e.g. 10–1,000 ppm. Higher concentrations are unlikely. Lower concentrations are not likely to cause the foaming problems which disrupt the efficiency of the process. Further, the bacterium is compatible with typical activated sludge microflora and should not therefore disrupt that ecological niche.

The population of *P. cepacia* OLSA100 which should be seeded in the activated sludge will depend on the residence time of the activated sludge. Residence times of from 24 hours to 96 hours have resulted in appreciable DODBS degradation in the presence of between $1 \times 10^7$ and $5 \times 10^7$ cells/milliliter. It is not suggested however that this particular cell concentration is essential. The measure is one of taking into account the DODBS concentration, residence time and such other factors which need consideration on a plant to plant basis. The criteria will be apparent to those skilled in the art given the goal of reducing the DODBS concentration to a level at which foaming is reduced preferably to the point at which foaming no longer occurs.

Aspects of the present invention are described hereinafter for the purpose of exemplification only.

EXAMPLE 1

Isolation of *P. cepacia* OLSA100

A sample of waste was taken from the wastewater treatment facility operated at Polysar Limited, at Sarnia, Ontario, and its microbial content was enumerated on pour plates using a bacterial medium solidified with agar (0.20%) containing 0.1% v/v DODBS as the sole carbon source and the basal salts composition shown in Table 1:

TABLE 1

| Chemical | Amount (grams/liter) |
|---|---|
| Na$_2$HPO$_4$ | 3.047 |
| KH$_2$PO$_4$ | 2.523 |
| Trinitriloacetic acid | 0.200 |
| MgSO$_4$ | 0.289 |
| CaCl$_2$.2H$_2$O | 0.067 |
| (NH$_4$)$_6$Mo$_7$O$_{24}$.4H$_2$O | 0.185 |
| FeSO$_4$.7H$_2$O | 0.002 |
| (NH$_4$)$_2$SO$_4$ | 1.000 |
| Sodium EDTA | 0.032 |
| ZnSO$_4$.H$_2$O | 0.00001 |
| MnSO$_4$.H$_2$O | 0.0015 |
| CuSO$_4$. 5H$_2$O | 0.00039 |
| Co(NO$_3$)$_2$.6H$_2$O | 0.00025 |

TABLE 1-continued

| Chemical | Amount (grams/liter) |
|---|---|
| $Na_2B_4O_7.H_2O$ | 0.0000002 |

(see Journal of General Microbiology, 43:159[1966])

The colonies which exhibited superior growth at 30° C. on the primary isolation medium after several days was transferred onto homologus medium by streaking for the isolation of single colonies. One of these replica colonies was transferred to a maintenance medium (plate count agar purchased from Di fco Inc., Detroit, Mich.) scraped into buffer and glycerol and stored at −20° C.. This culture, designated OLSA100, is the standard reference culture from which bacterial inoculum for all subsequent experiments was obtained.

Production of Bacteria for Degradation Studies

The culture was stored (in a frozen state) at approximately −20 C. A loop of the frozen reference culture was transferred to Plate Count Agar medium. The inoculated medium was placed in an incubator at 35° C. for a period of approximately 16 hours to grow the inoculum. From this growth, aqueous suspensions were prepared to inoculate liquid starter cultures of 25 ml. at a density of approximately $1 \times 10^8$ colony forming units/ml. These starter cultures were scaled up by inoculation of larger volumes at 0.5% inoculum with 16 hour inoculation of these larger cultures at 35° C.

Identification of Bacterial Strain OLSA100

The bacterium OLSA100 was Gram-strained and gave a negative reaction. The cellular morphology observed was similar in size and shape to that observed for a typical Pseudomonas cepacia bacterial strain (ATCC 25609). Ciochemical tests were done using the "NFT" procedure (kit available from Analytab Inc., Cleveland, Ohio). The results of determinations using this identification scheme are shown in Table 2, below:

TABLE 2

NFT Test Results

| NFT-test performed | Bacterium OLSA100 |
|---|---|
| Nitrate reduction | + |
| Tryptophanase reaction | − |
| Glucose fermentation | − |
| Arginine dihydrolase activity | − |
| Urease reaction | − |
| Esculin hydrolysis | − |
| Gelatinase reaction | − |
| Beta-galactosidase reaction | − |
| Assimilation tests | |
| D-glucose | + |
| L-arabinose | + |
| D-mannose | + |
| D-manitol | + |
| N—acetyl glucosamine | + |
| Maltose | + |
| D-gluconate | + |
| Caprate | − |
| Adipate | − |
| L-malate | + |
| Citrate | + |
| Phenylacetate | + |
| Oxidase reaction | + |

It was confirmed, therefore that the bacterium identified as OLSA100 belongs to the species Pseudomonas cepacia. Since the archetype P. cepacia ATCC 25609 was unable to grow on DODBS, however, it is conceivable that P. cepacia OLSA100 represents a unique strain of the species.

EXAMPLE 2

To test qualitatively for the ability of P. cepacia OLSA100 to degrade DODBS a faintly turbid aqueous suspension of the bacterium was prepared from a culture freshly grown on Plate Count Agar, a 0.2 ml aliquot of which was inoculated into 200 ml of the primary isolation medium listed above which also contained glucose (0.3%) and DODBS (500 ppm). These cultures were grown with aeration of a gyrotory shaker mechanism at 30° C.

Initially, samples were taken at various times after inoculation of the liquid culture and culture filtrates were scanned for the removal of DODBS. The degradation of DODBS was measured using a methylene blue assay test which is described below. The results of the experiment are shown in Table 3. The results show that significant amounts of DODBS are degraded by P. cepacia OLSA100 bacteria, in the presence of a glucose carbon source.

The following results were obtained:

TABLE 3

| Treatment Time | Percent DODBS removed |
|---|---|
| 24 h | 42 |
| 96 h | 59 |

A miniaturized methylene blue hydrochloride, dye-binding assay was used to measure DODBS concentrations in accordance with the following procedural steps:

1. add 5 ml sample containing DODBS to a test tube.*
2. add 1 ml methylene blue (MB) solution.**
3. wait 5 minutes for MB-complexes to form.
4. add 2.5 ml $CHCl_3$ reagent; mix well.
5. allow phases to separate.
6. with pasteur pipet, remove $CHCl_3$ (bottom) layer to a clean test tube.
7. add another 2.5 ml to the original MB-sample solution; mix well.
8. allow phases to separate.
9. with a pasteur pipet, remove $CHCl_3$ phase and combine it with the previously-extracted $CHCl_3$ layer.
10. measure the absorbance at 653 nanometers on an spectrophotometer. These measurements should be made within one hour, since the MB colour complexes tend to fade.

Notes to the methylene blue test:

A. The methylene blue solution was prepared as follows:
(1) dissolve 0.1 gm Methylene Blue Chloride in 100 ml $H_2O$.
(2) transfer 30 ml of this solution to a 1-liter flask.
(3) add 500 ml $H_2O$.
(4) add 7 ml of concentrated $H_2SO_4$+50 gm $NaH_2PO_4.H_2$
(5) shake until solution is complete.
(6) dilute to 1-liter with $H_2O$.

B. The absorbance of solutions of known DODBS concentration was measured for solutions prepared as follows:
1. add 1 ml DODBS to 99 ml of distilled water (rinse the pipet 5 times after adding the concentrated DODBS, by drawing the solution up and down the pipet)+10,000 ppm DODBS solution.

2. add 1 ml of the 10,000 ppm DODBS solution to 99 ml of distilled water; mix well, to make this 100 ppm DODBS solution.
3. in sterile test tubes, mix the following:

| H2O (ml) | 100 ppm DODBS (ml) | [DODBS], ppm |
|---|---|---|
| 5.0 | 0.0 | 0 (blank) |
| 4.9 | 0.1 | 10 |
| 4.8 | 0.2 | 20 |
| 4.7 | 0.3 | 30 |
| 4.6 | 0.4 | 40 |
| 4.5 | 0.5 | 50 |
| 4.4 | 0.6 | 60 |
| 4.3 | 0.7 | 70 |
| 4.2 | 0.8 | 80 |

C. The "5 ml sample" referred to in step 1 was prepared as follows:

Each 5 ml sample (step 1 of MB procedure) is a combination of 1 ml of sample (diluted if necessary) and 4 ml of distilled water. A "blank"—5 ml of distilled water—should be assayed with each set of controls or samples run through this procedure, to rezero the spectrophotometer. Correlate the absorbancy read for a sample with the ppm DODBS content on the standard curve. By multiplying this value by the dilution factor of the sample, the concentration of DODBS is determined.

Any sample containing an unknown amount of DODBS must be diluted in $H_2O$ and run through the procedure so that its concentration, as measured at 653 nm, falls in the range of the known DODBS standards. For example, a sampel was prepared which contained 0.05% v/v (500 ppm) DODBS originally. To determine if any change had occurred in the DODBS concentration at a later time, the 5 ml sample was composed of: 1 ml of a 1/20 dilution of the 0.05% DODBS solution +4 ml distilled $H_2O$. This 1/20 dilution in $H_2O$ of the 0.05% DODBS solution brings the concentration down to 0.0025% (25 ppm), which is in the range of the concurrently tested standards.

Before adding MB to the 5 ml sample, the pH of the sample should be near neutrality. This can be checked by:
(1) add 1 drop phemolphthalein indicator solution (5 g/liter).
(2) add sodium hydroxide solution (10 g/liter) dropwise until a pink colour develops.
(3) add sulfuric acid solution (7 ml concentrated $H_2SO_4$ + 993 ml $H_2O$) dropwise until the pink colour disappears. Continue with the procedure.

For all samples checked, the pH was at or near neutral. When checking multiple samples which are diluted and ready to run through the MB procedure, it was found that repetitive pH indicator tests are unnecessary.

EXAMPLE 3

An experiment was completed to qualitatively determine the compatability of the *P. cepacia* OLSA 100 bacterium with the bacteria contained in the activated sludge of the wastewater treatment facility operated by Polysar Limited at Sarnia, Ontario.

A sample of activated sludge was taken from the aforesaid wastewater treatment facility. 2000 ml of this sludge was diluted with 2000 ml of distilled water and the resulting mixture was placed in a laboratory respirometer. DODBS surfactant (10 ppm) and approximately 10 ppm of a defoaming agent were also added to the respirometer. The respiration rate of the activated sludge was then monitored over a 26 hour period, giving a respiration profile which was used as a reference profile for the second part of the experiment.

The second part of the experiment was completed by adding a mixture comprising 2000 ml of activated sludge from the aforesaid wastewater treatment facility, 2000 ml of distilled water, 10 ppm DODBS and 10 ppm defoaming agent to a respirometer. The mixture was inoculated with 8 ml of Pseudomonas cepacia OLSA 100 bacteria (containing approximately $2 \times 10^{10}$ colony forming units).

The respiration rate of the inoculated mixture was monitored over a 96 hour period, giving a respiration profile for the inoculated sludge. This respiration profile was similar to the reference respiration profile, indicating that the *P. cepacia* OLSA 100 bacterium is compatible with the activated sludge.

EXAMPLE 4

Four experiments were performed to demonstrate the DODBS-degrading activities of the cultures containing *P. cepacia* OLSA 100 bacteria during liquid culture and to provide a qunatitative measure of this degradative activity in the presence and absence of activated sludge taken from the wastewater treatment facility operated by Polysar Limited, at Sarnia, Ontario.

The mineral salts component for these trials is different from that used previously to demonstrate that another salts formulation would be successful in promoting the activity of *P. cepacia* OLSA 100. This formulation, called "Burks" salts (Journal of Bacteriology 125:1080 is shown in Table 4.

TABLE 4

| Chemical | Amount (grams/liter) |
|---|---|
| $KH_2PO_4$ | 2.735 |
| $K_2PO_4$ | 5.205 |
| $MgSO_4.7H_2O$ | 0.1995 |
| $CaCl_2$ | 0.0995 |
| $FeSO_4.H_2O$ | 0.00005 |
| $NaMoO_4.H_2O$ | 0.00025 |
| $(NH_4)_2SO_4$ | 1.0 |
| Glucose | 3.0 |

The following procedure was used for each of the experiments.
1. A "working mixture" (having a composition as indicated in Table 5 below) was added to a 1 l Erlenmeyer flask.
2. The flask was agitated in a rotary shaker for 72 hours.
3. The DODBS concentration was measured after 72 hours.

TABLE 5

| Flask | OLSA100 Added | Activated Sludge Added | DODBS (ppm) Initial | DODBS (ppm) at 72 hrs. | % Removal |
|---|---|---|---|---|---|
| A | No | Yes | 130 | 130 | |
| B | Yes | Yes | 130 | 91 | 30% |
| C | No | No | 130 | 130 | |
| D | Yes | No | 130 | 75 | 42% |

The results of the above experiment show the following:
(1) The experiment in flask A demonstrates that the bacteria contained in the activated sludge will not degrade DODBS.

(2) The experiment in flask B demonstrates that *Pseudomonas cepacia* OLSA 100 will degrade DODBS in the presence of the activated sludge.

(3) The experiment in flask C demonstrates that DODBS will not degrade by itself.

(4) The experiment in flask D demonstrates that *Pseudomonas cepacis* OLSA100 will degrade DODBS in the absence of activated sludge.

What is claimed is:

1. A process for degrading a non-halogenated surfactant compound of the formula

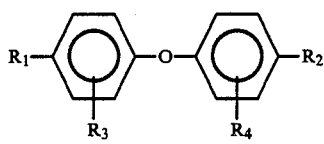

wherein $R_1$ and $R_2$ are independently selected from hydrogen and a $C_8$-$C_{20}$ alkyl radical and $R_3$ and $R_4$ are independently selected hydrogen and a hydrophilic radical selected from a sulfonate radical and a sultate radical, where one of $R_1$ and $R_2$ and one of $R_3$ and $R_4$ is other than hydrogen, said process comprising:

(i) providing wastewater containing said surfactant compound, (ii) preparing a pure culture of the bacterium *Pseudomonas cepacia* OLSA 100 (ATCC 53554)

(iii) introducing said wastewater and said bacterium into an aerobic wastewater treatment facility, and (iv) growing the bacterium *Pseudomonas cepacia* OLSA 100 (ATCC 53554) in said wastewater treatment facility under aerobic conditions so as to degrade said surfactant.

2. The process according to claim 1 wherein said compound is sodium dodecyl oxydibenzene disulfonate.

3. The process according to claim 2 wherein the *Pseudomonas cepacia* OLSA 100 (ATCC 53554) bacterium population is greater than $5 \times 10^7$ colony forming units per millilitre of wastewater.

4. The process according to claim 3 wherein the compound is present in the wastewater at a concentration ranging from 10 to 2,000 ppm.

* * * * *